United States Patent [19]

Schumacher et al.

[11] Patent Number: 4,975,279

[45] Date of Patent: Dec. 4, 1990

[54] METHOD OF IMPROVING POST-ISCHEMIC MYOCARDIAL FUNCTION USING A THROMBOXANE A2 ANTAGONIST IN COMBINATION WITH A THROMBOLYTIC AGENT AND COMBINATION

[75] Inventors: William A. Schumacher, Newtown, Pa.; Gary J. Grover, Stockton, N.J.

[73] Assignee: E. R. Squibb & Sons, Inc., Princeton, N.J.

[21] Appl. No.: 419,300

[22] Filed: Oct. 10, 1989

[51] Int. Cl.$^5$ .................. A61K 37/54; A61K 37/547; A61K 31/41; A61K 31/435

[52] U.S. Cl. .................... 424/94.63; 424/94.64; 514/381; 514/277

[58] Field of Search .............. 514/381, 2, 277; 424/94.63, 94.64

[56] References Cited

U.S. PATENT DOCUMENTS

| | | | |
|---|---|---|---|
| 4,661,469 | 4/1987 | Sarnoff | 514/2 |
| 4,663,336 | 5/1987 | Nakane et al. | 514/381 |
| 4,839,384 | 6/1989 | Ogletree | 514/381 |

OTHER PUBLICATIONS

Hoeft, A., et al., "Preservation of Myocardium in Transient Ischemia by the Thromboxane Synthetase Inhibitor UK-38, 485", *Res. Exp. Med.*, 1986; 186:35-46.
Schror, K., et al., "Treatment of Acute Myocardial Ischemia with a Selective Antagonist of Thromboxane Receptors (BM13,177)", *Br. J. Pharmacol.*, 1986; 87:631-7.
Schmitz, J. M., et al., "Vascular Prostaglandin and Thromboxane Production in a Canine Model of Myocardial Ischemia", *Circ. Res.*, 1985; 57:223-31.
Michael, L. H., et al., "Myocardial Ischemia: Platelet and Thromboxane Concentrations in Cardiac Lymph and the Effects of Iduprofen and Prostacyclin", *Circ. Res.*, 1986; 59:49-55.
Schumacher et al., *J. Pharmacol. Exp. Ther.*, 277:719 (1983).
Aiken et-al., *J. Pharmacol. Exp. Ther.*, 219:299 (1981).
Schumacher et al., J. Cardiol. Pharmacol, 7:739 (1985).
Mickelson, J. K. et al., Am. Heart J., Jun., 1987, pp. 1345-1352.
Lefer, A. M., et al., "Potentiation of Myocardial Salvage by Tissue Type Plasminogen Activator in Ischemic Cat Myocardium", *Circ. Res.*, vol. 63, No. 3, Sep. 1988.

*Primary Examiner*—Douglas W. Robinson
*Assistant Examiner*—Kevin Weddington
*Attorney, Agent, or Firm*—Burton Rodney

[57] ABSTRACT

A method is provided for improving post-ischemic myocardial function such as contractile dysfunction or reperfusion injury by administering a thromboxane receptor antagonist which is a 7-oxabicycloheptane substituted diamide prostaglandin analog in combination with a thrombolytic agent before, during or immediately after an ischemic attack.

11 Claims, No Drawings

METHOD OF IMPROVING POST-ISCHEMIC MYOCARDIAL FUNCTION USING A THROMBOXANE A2 ANTAGONIST IN COMBINATION WITH A THROMBOLYTIC AGENT AND COMBINATION

FIELD OF THE INVENTION

The present invention relates to a method for improving post-ischemic myocardial function in mammalian species by administering a thromboxane $A_2$ receptor antagonist which is a 7-oxabicycloheptane substituted diamide prostaglandin analog, in combination with a thrombolytic agent, such as t-PA, and to such combination of thromboxane $A_2$ receptor antagonist and thrombolytic agent.

BACKGROUND OF THE INVENTION

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow, for example, by thrombolysis or following transient ischemia, can prevent or mitigate the degree of cell death (infarction) occurring, reperfusion can still result in some degree of cardiac dysfunction or cell death (also referred to as stunned myocardia). Thus, it would be of great clinical value to find a means to preserve reperfusion function of the heart.

Thromboxane $A_2$ (TXA) which is released from the heart during reperfusion is thought to have physiological effects that may adversely influence myocardial performance, namely, TXA contributes to post ischemic contractile dysfunction, Hoeft, A., et al, "Preservation of myocardium in transient ischemia by the thromboxane synthetase inhibitor UK-38,485." Res. Exp. Med. 1986; 186:35–46, and Schror, K., et al, "Treatment of acute myocardial ischemia with a selective antagonist of thromboxane receptors. (BM 13,177)" Br. J. Pharmacol. 1986; 87:631–7.

Hoeft et al, supra, and Schror et al, supra, demonstrate the ability of certain TXA inhibitors and antagonists to reduce the severity of ischemia in some experimental models, though the physiological mechanisms of action of these compounds on post-ischemic recovery of function are still unknown. For instance, it is thought that TXA is released during ischemia as well as during reperfusion and thus TXA antagonists may be working during coronary occlusion, Schmitz, J. M., et al, "Vascular prostaglandin and thromboxane production in a canine model of myocardial ischemia." Circ. Rec. 1985; 67:223–31, Michael, L. H., et al, "Myocardial ischemia: platelet and thromboxane concentrations in cardiac lymph and the effects of ibuprofen and prostacyclin." Circ. Res. 1986; 59:49–55.

Available therapies for reperfusion of occluded blood vessels include intravenous or intracoronary administration of a plasminogen activator, i.e., thrombolytic therapy. Examples of plasminogen activators used in thrombolytic therapy are streptokinase, urokinase and tissue plasminogen activator (t-PA).

Thrombolytic therapy at best, even using the preferred t-PA, can only re-establish antegrade flow in an infarcted artery. Thrombolytic therapy will not reverse the factors responsible for initiation of the thrombus such as advanced atherosclerotic plaques, intimal rupture, enhanced platelet adherence and aggregability or coronary spasm. Patients with a residual stenosis of greater than 80%, after successful recanalization with t-PA, are at an extremely high risk of rethrombosis even in the presence of high dose heparin. In addition to persistent reocclusion, systemic bleeding can be associated with administration of high doses of t-PA.

Thromboxane synthetase inhibitors have been demonstrated to be efficacious in inhibiting platelet aggregation in various animal models of platelet activation. See Schumacher et al, J. Pharmacol. Exp. Ther. 227:790 (1983). Aiken et al, J. Pharmacol. Exp. Ther. 219:299 (1981) demonstrated that endogenous prostacyclin contributed to the efficacy of thromboxane synthetase inhibition via diversion or "steal" of platelet-derived endoperoxides to form prostacyclin.

Schumacher et al, J. Cardiol. Pharmacol. 7:739 (1985), report that prostacyclin augments streptokinase-induced coronary thrombolysis in the dog.

Mickelson, J. K. et al, Am. Heart J., June, 1987, p. 1345-1352, reports that CGS 13080, a thromboxane synthetase inhibitor, inhibits reocclusion following streptokinase-induced reperfusion after thrombotic occlusion of the circumflex coronary artery in a dog model.

European patent application No. 0265129A1 published Apr. 27, 1988, discloses a thrombolytic therapy which is a combination of a plasminogen activator and an agent which lowers the effective plasminogen activator dose requirement and which results in a lower incidence of reocclusion, which agent is an inhibitor of thromboxane activity, that is inhibits thromboxane-induced platelet aggregation. Such agents which inhibit thromboxane-induced platelet aggregation include thromboxane synthetase inhibitors and antagonists of platelet thromboxane receptors; thromboxane receptor antagonists disclosed include: EP045 and EP092 [Armstrong et al, Br. J. Pharmacol. 84:595 (1985)];

4-[2-(benzenesulfonamido)ethyl]phenoxyacetic acid (BM 13,177) [Patscheke et al, Thromb. Res. 33:277 (1984); U.S. Pat. No. 4,433,477];

4-[2-(phenylsulfonylamino)ethyl]phenoxyacetic acid (BM 13,505) [Stegmeier et al, Proc. EDTA ERA 22:1012 (1985) U.S. Pat. No. 4,258,058];

N,N'-[7-(3-chlorobenzene aminosulfonyl)-1,2,3,4-tetrahydroisoquinolyl]disulfonamide (SKF 88046) [Weichman et al, Prostaglandins Leukotrienes Med 15:167 (1984);

SQ29548 [1S-[1α,2β(5Z), 3β,4α]]-7-[3-[[2-phenylamino)carbonyl]hydrazino]methyl]-7-oxabicyclo[2.2.1]hept-2-yl]-5-heptenoic acid [Ogletree et al, J. Pharmacol. Exp. Ther. 234:435 (1985)];

AH23848 [Brittain et al, Circ. 72:1208 (1985)];

13APA [LeBreton et al, Proc. Natl. Acad. Sci. U.S.A. 76:4097 (1979)]; and

ON03708 Kutsura et al, Adv. Pros. Thromb. LK. Res. 11:351 (1983)].

Plasminogen activators disclosed in European 0265129A1 include streptokinase (SK), urokinase (UK) and tissue plasminogen activator (tPA), as well as related fibrinolytics such as acylated plasminogen streptokinase activator complex, prourokinase, single chain urokinase (SCUPA), antibody-bound plasminogen activators and hybrid tPA-UK proteins and other so-called "third generation" thrombolytics.

Lefer, A. M. et al, "Potentiation of Myocardial Salvage by Tissue Type Plasminogen Activator in Combination with a Thromboxane Synthetase Inhibitor in Ischemic Cat Myocardium" *Circ. Res.* Vol. 63, No. 3, Sept. 1988, discloses the use of a combination of tissue type plasminogen activator and a thromboxane synthetase inhibitor (CGS-13080) to preserve myocardial integrity in animals subjected to acute myocardial ischemia.

U.S. Patent No. 4,661,469 to Sarnoff discloses that the absorption rate of t-PA in the blood is enhanced by utilizing with the t-PA dosage, a dosage of an absorption enhancing agent for t-PA, preferably hydroxylamine hydrochloride, as well as ammonia, ammonium salts, urea and derivatives thereof, and alkyl and aryl hydroxylamines. In Column 12, starting at line 39, it is indicated that "It has also been found that to prevent reocclusions or platelet aggregation it is desirable to either:

1. inhibit synthesis of thromboxane A (thromboxane $A_2$) with a thromboxane synthetase inhibitor, e.g. an imidazole such as 4-(2-[1H-imidazol-1-yl)ethoxy)benzoic acid, hydrochloride (dazoxiben);

2. introduce an antagonist for the receptor of the thromboxane A (thromboxane $A_2$) such as [$1\alpha,2\beta(5Z),3\beta(1E),4\alpha$]-7-[3-(3-cyclohexyl-3-hydroxy-1-7-oxabicyclo[2.2.1]hept-2-yl]-5-heptenoic acid) (SQ27,427);

3. introduce another inhibitor of platelet aggregation, e.g aspirin, indomethacin, naproxin, and sulfinpyrazone."

DESCRIPTION OF THE INVENTION

In accordance with the present invention, a method is provided for treating post-ischemic myocardial dysfunction in mammalian species to improve heart function, wherein a therapeutically effective amount of a thromboxane $A_2$ receptor antgonist, which is a 7-oxabicycloheptane substituted diamide prostaglandin analog, in combination with a thrombolytic agent is systemically administered, such as orally or parenterally, or locally to the heart, for example, by catheter, prior to, during or soon after reperfusion, that is, within 9 hours, preferably within 3 to 5 hours of a myocardial infarction, to mitigate the post-ischemic adverse effects on heart function during periods of myocardial occlusion and reperfusion.

The term "reperfusion" is employed herein to refer to release of occlusion and resumption of blood flow.

In addition, in accordance with the present invention, there is provided a combination of a 7-oxabicycloheptane substituted diamide prostaglandin analog and thrombolytic agent.

The 7-oxabicycloheptane substituted diamide prostaglandin analog and thrombolytic will be employed in a weight ratio to each other of within the range of from about 0.1:1 to about 10:1 and preferably from about 0.4:1 to about 2.5:1.

It has been found that the combination of 7-oxabicycloheptane substituted diamide prostaglandin analog with a thrombolytic agent improves postischemic performance of the heart by improving postischemic contractile function when administered during both the coronary occlusion period and the reperfusion period (preferably within the first 3 to 5 hours after myocardial infarction or as soon after the myocardial infarction as possible) or only during the reperfusion period. Such improvement in post-ischemic performance of the heart is evidenced by decreased contractile dysfunction, decrease in tissue necrosis, reduced myocardial workload, reduced myocardial demand for oxygen and reduced myocardial peripheral work.

The above combination may also be administered in the weeks and months following myocardial infarction to inhibit left ventricle chamber enlargement and wall thinning.

The above benefits are achieved through use of a 7-oxabicycloheptane substituted diamide prostaglandin analog in conjunction with a thrombolytic agent. The combination of the invention will prevent reperfusion injury which develops when blood flow is restored to a previously ischemic area with little or no lytic effect.

While use of a thrombolytic agent alone such as t-PA may reduce infarct size but at the risk of producing a severe lytic effect, that is a breakdown of clotting factor in the blood, the combination of the invention will reduce infarct size when administered in accordance with the present invention, will have little or no lytic effect.

The 7-oxabicycloheptane substituted diamide prostaglandin analogs employed herein are disclosed in U.S. Patent No. 4,663,336 to Nakane et al, which have the structural formula

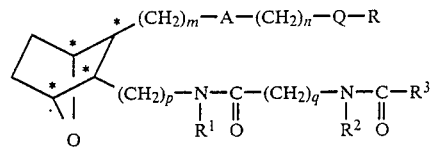

including all stereoisomers thereof, wherein m is 0 to 4; A is —CH=CH— or —CH$_2$—CH$_2$—; n is 1 to 5; Q is —CH=CH—, —CH$_2$—,

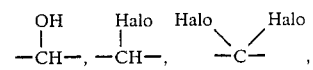

or a single bond; R is $CO_2H$, $CO_2$alkyl, $CO_2$ alkali metal, $C_2$polyhydroxyamine salt, —CH$_2$OH,

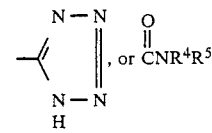

$R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, arylalkyloxy, aryloxy, amino, alkylamino, arylalkylamino, arylamino, lower alkyl-S—, aryl-S—, arylalkyl-S—, aryl-S-alkyl-,
     $\overset{(O)_{n'}}{\|}$         $\overset{(O)_{n'}}{\|}$         $\overset{(O)_{n'}}{\|}$         $\overset{(O)_{n'}}{\|}$

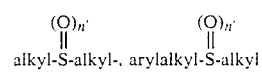

(wherein n' is 0, 1 or 2), alkylaminoalkyl, arylaminoalkyl, arylalkylaminoalkyl, alkoxyalkyl, aryloxyalkyl or arylalkoxyalkyl.

[(1S-[1$\beta$,2$\alpha$(5Z),3$\alpha$,4$\beta$]]-7-[3-[[[[(1-oxo-heptyl)amino]acetyl]amino]methyl]-7-oxabicyclo-[2.2.1]hept- 2-yl]-5-heptenoic acid (SQ30,741) and the corresponding tetrazole, and [1S-[1β(Z),2β(Z),3β,4α]]-7-[3-[[[[(4-cyclohexyl-1oxobutyl)amino]amino]methyl]-7-oxabicyclo-[2.2.1]hept-2-yl]-5-heptenoic acid are preferred. Most preferred is SQ30,741.

The disclosure of the above-mentioned U.S. patent is incorporated herein by reference.

Thrombolytic agents which may be employed herein include tissue plasminogen activator (t-PA), recombinant t-PA, streptokinase, urokinase, prourokinase, and anisoylated plasminogen streptokinase activator complex (APSAC, Eminase, Beecham Laboratories).

Preferred is a combination of SQ30,741 and t-PA.

In carrying out the method of the present invention, the thromboxane $A_2$ receptor antagonist in combination with the thrombolytic agent may be administered to mammalian species, such as monkeys, dogs, cats, humans, etc. during the period of coronary occlusion and/or during the period of reperfusion and/or shortly after termination of the ischemic attack, for example preferably within 3 to 5 hours and most preferably within 1 to 2 hours after the ischemia, within 24 to 48 hours after the ischemia and for weeks and months thereafter.

Although the above combination may be administered systemically, such as orally or parenterally, within 1 hour after the ischemia, it is preferred that the combination be administered locally, as soon after the ischemic attack as possible, to the coronary arteries by catheter such as by arterial angiography or intracoronary injection or by cardioplegic solution by the aortic route.

With regard to dosage of the combination, where the drug is administered by arterial angiography, intracoronary injection or intravenously, thromboxane $A_2$ receptor antagonist will be employed in an amount from about 0.005 to about 30 mg/kg/ treatment and preferably from about 0.01 to about 3 mg/kg/treatment will be employed. The number of treatments will depend upon the length of the ischemic attack and the progress of reperfusion to achieve normal heart function. Usually, from 1 to 5 treatments per day will be required for as long as contractile dysfunction continues.

The thrombolytic agents will be employed in amounts as indicated in the Physician's Desk Reference (PDR), 43rd Edition, 1989, Thus, Hoechst-Roussel's Streptase ® brand of streptokinase may be administered as follows:

TABLE I

Suggested Dilutions and Infusion Rates

| Streptase ® (streptokinase) Dosage/Infusion Rate | Streptase ® (streptokinase) Vial Content Needed | Total Volume of Solution (mL) | Infusion Pump Rate |
|---|---|---|---|
| I. Intracoronary Artery Administration | | | |
| A. Bolus Infection 20,000 IU | 1 vial, 250,000 IU* | 125 | Inject 10 mL |
| B. Maintenance Dose 2,000 IU/min | | | 60 mL per hour |
| *sufficient for Bolus Injection and Maintenance Dose | | | |
| II. Intravenous Administration | | | |
| A. Loading Dose 250,000 IU/30 min | (a) 1 vial, 250,000 IU or | 45 | 90 mL per hour for 30 min |
| | (b) 1 vial, 750,000 IU | 45 | 30 mL per hour for 30 min |
| B. Maintenance Dose 100,000 IU/hr | 1 vial, 750,000 IU | 45** | 6 mL per hour |

**If necessary, total volume may be increased, in increments of 45 mL, to a maximum of 500 mL with the infusion pump rate increased accordingly. The total volume of 45 mL or multiple thereof is recommended.

For example, streptokinase may be administered intravenously in amounts of about $5 \times 10^4$ to $3 \times 10^6$ IU per patient over 0.25 to 6 hours.

t-PA employed herein may be Genentech's Activase ®, Alteplase which, as described, in the Physician's Desk Reference (PDR), 43 Ed., 1989, page 988 is as follows.

ACTIVASE ®, Alteplase, a sterile, white to off-white, lyophilized powder, is intended for intravenous administration after reconstitution with sterile water for injection, USP. The quantitative composition of the lyophilized product is:

| 50 mg (29 million IU) Vial | 20 mg (11.6 million IU) Vial |
|---|---|
| Alteplase 50 mg (29 million IU) | Alteplase 20 mg (11.6 million IU) |
| L-Arginine 1.7 g | L-Arginine 0.7 g |
| Phosphoric Acid 0.5 g | Phosphoric Acid 0.2 g |
| Polysorbate 80, less than 4 mg | Polysorbate 80, less than 1.6 mg |

Phosphoric acid and/or sodium hydroxide may be used prior to lyophilization for pH adjustment.

Biological potency is determined by an in vitro clot lysis assay and is expressed in International Units as tested against the WHO standard. The specific activity of ACTIVASE ®, Alteplase, is 580,000 IU/mg.

The recommended dose is 100 mg administered as 60 mg (34.8 million IU) in the first hour (of which 6 to 10 mg is administered as a bolus over the first 1–2 minutes), 20 mg (11.6 million IU) over the second hour, and 20 mg (11.6 million IU) over the third hour. For smaller patients (less than 65 kg), a dose of 1.25 mg/kg administered over 3 hours, as described above, may be used.

A useful dose of t-PA in the method of the invention is of about 1 to about 75 mg per adult patient, preferably of about 2 to about 30 mg per adult patient, although higher doses such as up to 150 mg/kg is not precluded.

Abbott's Abbokinase brand of urokinase may be administered after heparin dosing of 2,500 to 10,000 units IV, in an amount by infusion into the occluded artery at a rate of 4 ml per minute (6,000 IU per minute) for periods of up to 2 hours.

Prourokinase may be administered in conventional dosages normally used in clinical practice such as a 7.5 mg bolus followed by 40.5 mg IV for 1 hour or 66.5 mg IV for 1 hour.

APSAC (Eminase) may be administered in conventional dosages normally used in clinical practice such as a single 30 unit IV dosage.

Where the combination is to be administered by angiography, intravenously, or intracoronary injection, it will be formulated in conventional vehicles, such as distilled water, saline, Ringer's solution, a cardioplegic salt solution or other conventional carriers.

The or combination may also be incorporated in a conventional dosage form, such as a tablet, capsule, elixir or injectable. The above dosage forms will also include the necessary carrier material, excipient, lubricant, buffer, antibacterial, bulking agent (such as mannitol), antioxidants (ascorbic acid of sodium bisulfite) or the like. Oral dosage forms are preferred, although parenteral forms are quite satisfactory as well.

With regard to such systemic formulations, single or divided doses of from about 5 to about 2500 mg, preferably from about 10 to 2000 mg/one to four times daily, may be administered in systemic dosage forms as described above for a period sufficient to restore normal heart function.

The dose administered must be carefully adjusted according to age, weight and condition of the patient, as well as the route of administration, dosage form and regimen and the desired result.

Thus, for oral administration, a satisfactory result may be obtained employing the thromboxane $A_2$ receptor antagonist in an amount within the range of from about 0.01 mg/kg to about 100 mg/kg and preferably from about 0.1 mg/kg to about 25 mg/kg in combination with the thrombolytic agent in an amount within the range of from about 0.01 mg/kg to about 100 mg/kg and preferably from about 0.1 mg/kg to about 25 mg/kg with the thromboxane $A_2$ receptor antagonist and thrombolytic agent being employed together in the same oral dosage form or in separate oral dosage forms taken at the same time.

A preferred oral dosage form, such as tablets or capsules, will contain SQ30,741 in an amount of from about 0.1 to about 500 mg, preferably from about 125 to about 200 mg, and more preferably from about 25 to about 150 mg, alone or with the thrombolytic agent (preferably t-PA) in an amount of from about 1 to about 350 mg, preferably from about 2 to about 200 mg, and more preferably from about 30 to about 150 mg.

For parenteral administration, the thromboxane $A_2$ receptor antagonist (preferably SQ30,741) will be employed in an amount in the range of from about 0.005 mg/kg to about 10 mg/kg and preferably from about 0.01 mg/kg to about 1 mg/kg, with the thrombolytic agent (preferably t-PA) in an amount within the range of from about 0.005 mg/kg to about 20 mg/kg and preferably from about 0.01 mg/kg to about 2 mg/kg.

The composition described above may be administered in the dosage forms as described above in single or divided doses of one to five times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

The following Examples represent preferred embodiments of the present invention.

EXAMPLE 1

An injectable solution for use in administering the thromboxane $A_2$ receptor antagonist ceranapril (SQ30,741) by intracoronary injection by arterial angiography or intravenously is produced as follows:

| | |
|---|---|
| SQ 30,741 | 500 mg |
| Methyl paraben | 5 mg |
| Propyl paraben | 1 mg |
| Sodium chloride | 25 g |
| Water for injection qs. | 5 l. |

The SQ30,741, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

The so-formed injectable solution of SQ30,741 may be employed in conjunction with conventional dosage forms of t-PA for reducing myocardial infarct size and improving post-ischemic contractive dysfunction.

EXAMPLE 2

An SQ30,741 formulation suitable for oral administration in improving post-ischemic contractile function is set out below.

1000 tablets each containing 100 mg of SQ30,741 were produced from the following ingredients.

| | | |
|---|---|---|
| SQ 30,741 | 100 | g |
| Corn starch | 50 | g |
| Gelatin | 7.5 | g |
| Avicel (microcrystalline cellulose) | 25 | g |
| Magnesium stearate | 2.5 | g |

The SQ30,741 and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for improving post-ischemic contractile function.

The above tablets for use in administering SQ30,741 may be employed in conjunction with conventional dosage forms of tPA for reducing myocardial infarct size and improving post-ischemic contractile dysfunction.

EXAMPLE 3

An injectable solution for use in administering SQ30,741 and thrombolytic agent by intracoronary injection, by arterial angiography or intravenously containing SQ30,741 and streptokinase (conventional dosage) as the thrombolytic agent is prepared as described in Example 1.

EXAMPLE 4

An injectable for use in improving postischemic contractile dysfunction is prepared as described in Example 1 except that the thrombolytic agent employed is urokinase.

EXAMPLE 5

An injectable for use in improving postischemic contractile dysfunction is prepared as described in Example 1 except that the thromboxane $A_2$ antagonist employed is [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic acid. This injectable is used together with t-PA as described in Example 1.

EXAMPLE 6

A bicarbonate buffered physiological (cardioplegic) salt solution (PSS) is prepared containing, in mM: 118.4 NaCl, 4.7 KCL, 1.2 $KH_2PO_4$, 1.2 $MgSO_4$, 2.5 $CaCl_2$, 25.0 $NaHCO_3$ and 11.7 glucose. SQ30,741 (50 mg) is added to the salt solution (0.5 l) which solution may be administered by the aortic route and used with t-PA for reducing myocardial infarct size and improving post-ischemic contractile dysfunction.

EXAMPLE 7

The following experiment was carries out to show that the thromboxane ($TxA_2$) receptor antagonist SQ30,741 may be used to improve the efficacy of the thrombolytic t-PA, and that t-PA can potentiate the anti-ischemic effects of SQ30,741.

Anesthetized dogs were subjected to left circumflex coronary artery occlusion for 90 minutes and reperfusion for 5 hours. The dogs were treated during reperfusion with a dose of t-PA causing a 20-30% reduction in serum fibrinogen alone or in combination with 1.5 mg/kg+0.4 mg/kg/hour SQ30,741, starting 10 minutes after initiation of ischemia. At these doses, neither t-PA nor SQ30,741 alone significantly reduced infarct size (57±6, 50±10, 57±6% of the LV area at risk for vehicle, t-PA, SQ30,741 respectively) while combination treatment resulted in a significant reduction in infarct size (38±5% of the LV area at risk). Higher doses of t-PA and SQ30,741 alone significantly reduced infarct size. The protective effects of t-PA and SQ30,741 occurred without altering peripheral hemodynamic status. No differences in collateral or reperfusion blood flow in the ischemic region were observed between groups.

Thus, while SQ30,741 may act to improve the efficacy of thrombolysis, t-PA may in turn enhance the anti-ischemic activity of SQ30,741.

What is claimed is:

1. A method of improving post-ischemic myocardial function in a mammalian species, which comprises administering to a mammalian species in need of such treatment a therapeutically effective amount of a 7-oxabicycloheptane substituted diamide prostaglandin analog which is [(1S-[1η,2∞(5Z), 3∞,4β]]-7-[3-[[[(1-oxoheptyl)amino]acetyl]amino]methyl]-7-oxabicyclo-[2.2.1]hept2-yl]-5-heptenoic acid (SQ30,741) with a thrombolytic agent to reduce or eliminate reperfusion injury.

2. The method as defined in claim 1 wherein the combination of the 7-oxabicycloheptane substituted diamide prostaglandin analog and thrombolytic agent is administered by arterial angiography or by intracoronary injection, intravenously or orally.

3. The method as defined in claim 1 wherein the combination of the 7-oxabicycloheptane substituted diamide prostaglandin analog and thrombolytic agent is administered prior to, during or after reperfusion.

4. The method as defined in claim 1 wherein the combination of the 7-oxabicycloheptane substituted diamide prostaglandin analog and thrombolytic agent is administered during coronary occlusion and reperfusion.

5. The method as defined in claim 1 wherein the combination of the 7-oxabicycloheptane substituted diamide prostaglandin analog and thrombolytic agent is administered only during reperfusion.

6. The method as defined in claim 1 wherein the thrombolytic agent is tissue plasminogen activator (t-PA), recombinant tissue plasminogen activator, streptokinase, urokinase or prourokinase.

7. The method as defined in claim 6 wherein the thrombolytic agent is tissue plasminogen activator or recombinant tissue plasminogen activator.

8. A pharmaceutical combination useful for improving post-ischemic myocardial dysfunction comprising a 7-oxabicycloheptane substituted diamide prostaglandin analog which is [(1S-[1β, 2∞(5Z), 3∞, 4β]]-7-[3-[[[(1-oxoheptyl)amino]acetyl]amino]methyl]-7-oxabicyclo-[2.2.1]hept-2-yl]-5-heptenoic acid (SQ30,741) and a thrombolytic agent.

9. The combination as defined in claim 8 wherein the 7-oxabicycloheptane substituted diamide prostaglandin analog and thrombolytic agent are in a weight ratio to each other within the range of from about 0.1:1 to about 10:1.

10. The combination as defined in claim 9 wherein the thrombolytic agent is tissue plasminogen activator, recombinant tissue plasminogen activator, streptokinase, urokinase or prourokinase or anisoylated plasminogen streptokinase activator complex (APSAC).

11. The combination as defined in claim 10 wherein the thrombolytic agent is t-PA.

* * * * *